United States Patent
Trkovnik et al.

[11] Patent Number: 6,100,409
[45] Date of Patent: Aug. 8, 2000

[54] HYDROXY AND POLYHYDROXY DERIVATIVES OF COUMARIN, PREPARATION THEREOF AND ANTIVIRAL ACTION THEREOF

[75] Inventors: Mladen Trkovnik; Zrinka Ivezić, both of Zagreb, Croatia

[73] Assignee: PLIVA farmaceutska, kemijska, prehrambena i kozmeticka industrija dionicko drustvo, Zagreb, Croatia

[21] Appl. No.: 09/165,424

[22] Filed: Oct. 2, 1998

[30] Foreign Application Priority Data

Oct. 2, 1997 [HR] Croatia .................. P970529A

[51] Int. Cl.⁷ .................. C07D 311/16; A61K 31/352
[52] U.S. Cl. .................. 549/284; 514/457
[58] Field of Search .................. 514/457; 549/284

[56] References Cited

PUBLICATIONS

Mazumder et al., J. Med. Chem. 39(13), 2472–2481, 1996.
Zhao et al., J. Med. Chem 40(2), 242–249, 1997.

*Primary Examiner*—Johann Richter
*Assistant Examiner*—Taofiq A. Solola
*Attorney, Agent, or Firm*—Pollock, Vande Sande & Amernick

[57] ABSTRACT

The present invention relates to novel hydroxy and polyhydroxy derivatives of coumarin fused with dialdehydes and aldehyde acids of the general formulae I, II, III and IV:

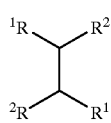

I

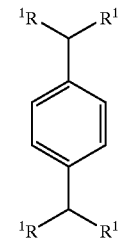

II

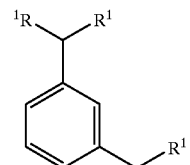

III

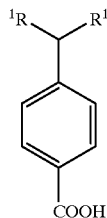

IV wherein
$R^1=R^2=$4-hydroxycoumarin;
$R^1=R^2=$4,7-dihydroxycoumarin;
$R^1=R^2=$4,5,7-trihydroxycoumarin;
$R^1=$4-hydroxycoumarin, $R^2=$—CH(OH)CH₃.

An object of the invention are also processes for the preparation of hydroxy and polyhydroxy derivatives of coumarin fused with dialdehydes and aldehyde acids, and the antiviral action thereof.

Novel hydroxy and polyhydroxy derivatives of coumarin according to the present invention exhibit antiviral action against HIV-1 virus.

2 Claims, No Drawings

HYDROXY AND POLYHYDROXY DERIVATIVES OF COUMARIN, PREPARATION THEREOF AND ANTIVIRAL ACTION THEREOF

TECHNICAL FIELD

IPC: C07D 311/04

In investigations in the field of finding novel compounds having antiviral action against HIV-1 and HIV-2 viruses causing AIDS disease, some derivatives of 4-hydroxycoumarin, e.g. phenoprocoumon, showed a significant action (H. I. Skulnick et al., *J. Med. Chem.* 40 (1997) 1149). This invention gave a strong push to further investigations of novel hydroxycoumarin derivatives, which resulted in the synthesis of 3,3',3",3'"-(1,4-dimethylenephenyl)tetrakis[4-hydroxycoumarin] having the activity $IC_{50}=1.5$ μM (H. Zhao et al., *J. Med. Chem.* 40 (1997) 242).

It should especially be pointed out that derivatives of hydroxycoumarin may be used as oral non-peptide inhibitors of HIV-1 protease and integrase and some of the said derivatives have reached the first phase and the second phase of clinical trials.

On the basis of their earlier experiences the present inventors have prepared a series of novel hydroxy and polyhydroxy derivatives of coumarin in order to find still more active preparations with expressed action against HIV-1 and HIV-2 viruses.

The present invention relates to novel hydroxy and polyhydroxy derivatives of coumarin fused with dialdehydes and aldehyde acids of the general formulae I, II, III and IV:

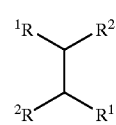

I

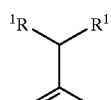

II

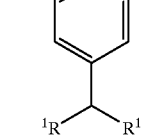

III

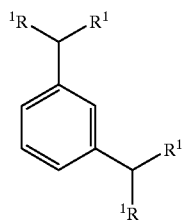

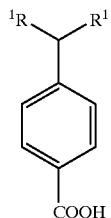

IV wherein $R^1=R^2$=4-hydroxycoumarin;

$R^1=R^2$=4,7-dihydroxycoumarin;

$R^1=R^2$=4,5,7-trihydroxycoumarin;

$R^1$=4-hydroxycoumarin, $R^2$=—CH(OH)CH$_3$.

Objects of the invention are also processes for the preparation of hydroxy and polyhydroxy derivatives of coumarin fused with dialdehydes and aldehyde acids, and the antiviral action thereof.

According to the present invention novel hydroxy and polyhydroxy derivatives of coumarin fused with dialdehydes and aldehyde acids of the general formulae I, II, III and IV are prepared starting from hydroxy- and polyhydroxycoumarin of the formula V

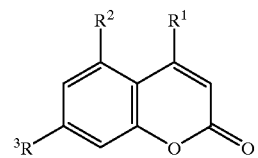

V wherein $R^1$=OH, $R^2=R^3$=H;

$R^1=R^3$=OH, $R^2$=H;

$R^1=R^2=R^3$=OH, by condensation reactions in ethanol or in glacial acetic acid with dialdehydes and aldehyde acids of the formulae VI, VII, VIII and IX:

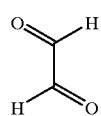

VI

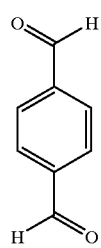

VII

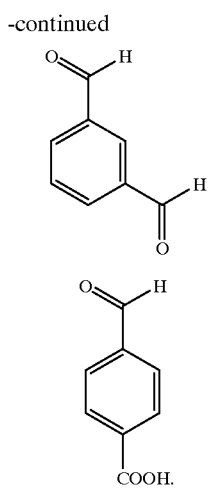

Novel hydroxy and polyhydroxy derivatives of coumarin according to the present invention exhibit antiviral action against HIV-1 virus.

The invention is illustrated by the following Examples, which in no way limit the scope thereof.

EXAMPLE 1

3,3',3'',3'''-ethylenetetrakis[4-hydroxycoumarin]

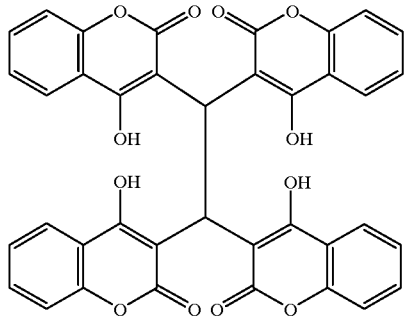

4-hydroxycoumarin (10.00 g; 61.7 mmol) was dissolved in glacial acetic acid (70.0 ml) and to this solution a 30% aqueous glyoxal solution (2.75 ml; 17.0 mmol) was added. The reaction mixture was heated at boiling temperature for 5 hours. Upon cooling a yellow precipitate (7.21 g; 70%) was obtained and it was recrystallized from glacial acetic acid. M.p. 298–300° C.

Analysis:

calculated for $C_{38}H_{22}O_{12}$: C=68.06; H=3.31.
found: C=68.33; H=3.12.
FABMS: m/z: 671 (M$^+$).
IR (KBr): v/cm$^{-1}$: 3447 (br); 1719; 1637; 1607; 761.

EXAMPLE 2

3,4-di(4-hydroxycoumarin)-hexane-2,5-diol

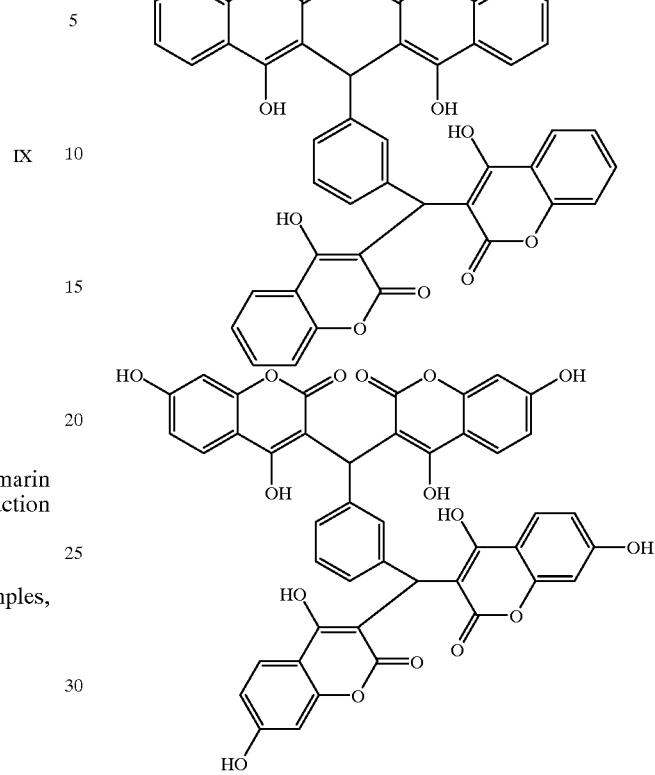

4-hydroxycoumarin (10.00 g; 61.7 mmol) was dissolved in 96% ethanol (50.0 ml) and to this solution a 30% aqueous glyoxal solution (2.75 ml; 17.0 mmol) was added. The reaction mixture was heated at boiling temperature for 15 minutes. The obtained white precipitate was filtered in vacuo and washed several times with hot 96% ethanol (6.05 g; 58%). M.p. 309–310° C.

Analysis:

calculated for $C_{24}H_{22}O_8$: C=65.75; H=5.06.
found: C=65.64; H=5.04.
FABMS: m/z: 439 (M$^+$).
IR (KBr): v/cm$^{-1}$: 3389 (br); 2981; 1721; 1669; 1640; 1236; 761.

EXAMPLE 3

3,3',3'',3'''-ethylenetetrakis[4,7-dihydroxycoumarin]

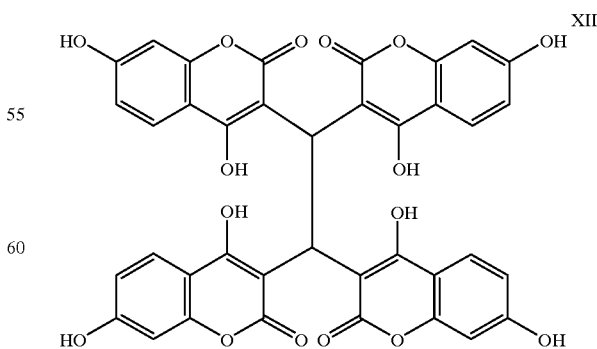

To a solution of 4,7-dihydroxycoumarin (2.50 g; 14.0 mmol) in absolute ethanol (10.0 ml) a 30% aqueous glyoxal solution (0.65 ml; 3.86 mmol) was added. The reaction mixture was heated at boiling temperature for 4 hours under discharging ethanol during the reaction, upon cooling it was left overnight at −13° C. and the obtained light yellow precipitate was filtered in vacuo (1.20 g; 47%). It was recrystallized from N,N-dimethylformamide/glacial acetic acid mixture (1:1). M.p.>300° C.

Analysis:

calculated for $C_{38}H_{22}O_{16}$: C=62.13; H=3.02.

found: C=62.39; H=2.65.

FABMS: m/z: 735 ($M^+$).

IR (KBr): $v/cm^{-1}$: 3435 (br); 1720; 1630; 1601; 760.

EXAMPLE 4

3,3',3'',3'''-ethylenetetrakis[4,5,7-trihydroxycoumarin]

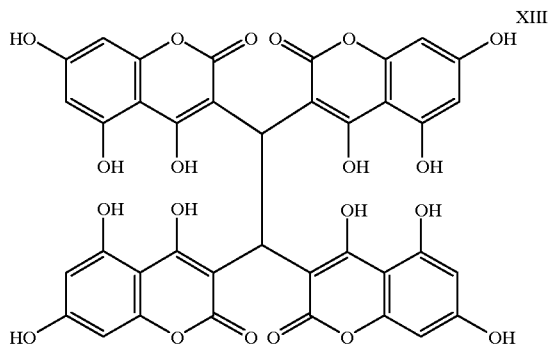

To a solution of 4,5,7-trihydroxycoumarin (2.00 g; 10.3 mmol) in absolute ethanol (10.0 ml) a 30% aqueous glyoxal solution (0.50 ml; 2.84 mmol) was added. The reaction mixture was heated at boiling temperature for 30 minutes and then evaporated to one third of the volume. To the residue in a flask a low-boiling petroleum ether was added and it was stirred for one hour at room temperature, whereat the gelatinous solution turned into a fine crystalline orange brown precipitate (1.44 g; 70%). It was recrystallized from a 96% ethanol/glacial acetic acid mixture (1:1). M.p.>300° C.

Analysis:

calculated for $C_{38}H_{22}O_{20}$ x $H_2O$: C=55.89; H=2.96.

found: C=55.53; H=3.32.

FABMS: m/z: 799 ($M^+$).

IR (KBr): $v/cm^{-1}$: 3423 (br); 2959; 1618; 1299; 1157; 761.

EXAMPLE 5

3,3',3'',3'''-(1,4-dimethylenephenyl)tetrakis[4,5,7-trihydroxycoumarin]

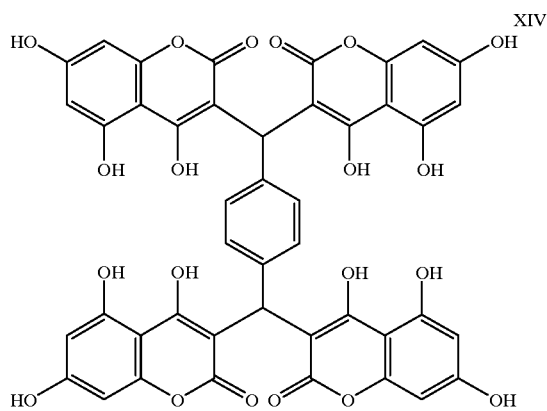

To a solution of 4,5,7-trihydroxycoumarin (3.00 g; 15.5 mmol) in 96% ethanol (15.0 ml) terephthaldialdehyde (0.57 g; 4.26 mmol) was added. The reaction mixture was heated at boiling temperature for 30 minutes and abundant gelatinous precipitate was formed. The obtained precipitate was filtered in vacuo and then transferred to a flask, into which also diisopropyl ether (30.0 ml) was added under stirring for one hour at room temperature. The obtained orange red precipitate was filtered off and dried (2.92 g; 86%). M.p. 228–230° C.

Analysis:

calculated for $C_{44}H_{26}O_{20}$: C=60.42; H=3.00.

found: C=60.37; H=2.76.

FABMS: m/z: 875 ($M^+$).

IR (KBr): $v/cm^{-1}$: 3380 (br); 1648; 1622; 1601; 1260; 760.

EXAMPLE 6

3,3',3'',3'''-(1,3-dimethylenephenyl)tetrakis[4,5,7-trihydroxycoumarin]

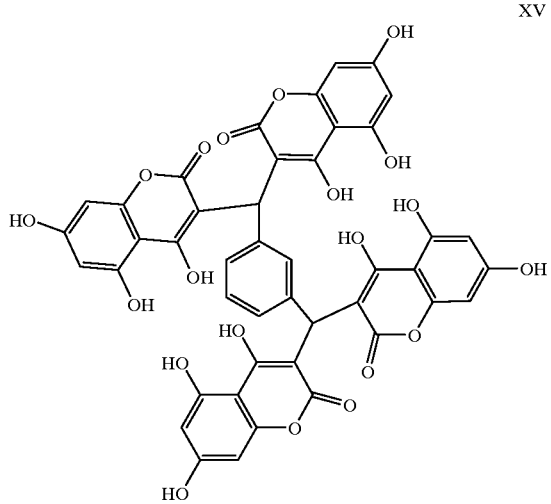

To a solution of 4,5,7-trihydroxycoumarin (3.00 g; 15.5 mmol) in 96% ethanol (15.0 ml) isophthaldialdehyde (0.57 g; 4.26 mmol) was added. The reaction mixture was heated at boiling temperature for 3.5 hours and abundant gelationous precipitate was formed. The obtained precipitate was filtered in vacuo and then transferred to a flask, into which also diisopropyl ether (150.0 ml) was added under stirring for 30 minutes at room temperature and then for another hour under reflux. The red brown precipitate obtained by cooling was filtered off and dried (3.33 g; 98%). M.p.>300° C.

Analysis:
calculated for $C_{44}H_{26}O_{20}$: C=60.42; H=3.00.
found: C=60.48; H=3.04.
FABMS; m/z: 875 (M⁺).
IR (KBr): v/cm⁻¹: 3374 (br); 1640; 1610; 1597; 1249; 761.

EXAMPLE 7
3,3'-(4-carboxybenzylidene)bis[4,7-dihidroxycoumarin]

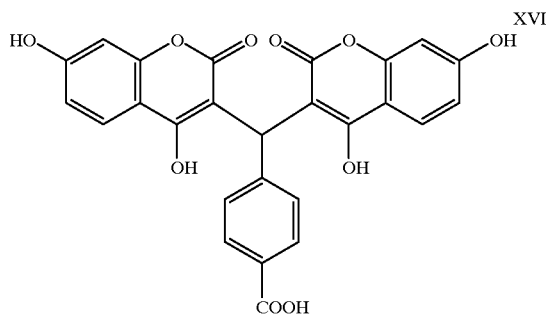
XVI

To a solution of 4,7-dihidroxycoumarin (4.00 g; 22.5 mmol) in 96% ethanol (50.0 ml) terephthalaldehyde acid (1.86 g; 1.24 mmol) was added. The reaction mixture was heated at boiling temperature for 8 hours. After cooling to room temperature the reaction mixture was evaporated to one half of its volume and left overnight at −13° C. After filtering in vacuo a pale yellow precipitate (2.84 g; 52%) was obtained and recrystallized from 20% ethanol. M.p. 239–242° C.

Analysis:
calculated for $C_{26}H_{16}O_{10} \times H_2O$: C=61.66; H=3.58.
found: C=61.32; H=3.56.
FABMS: m/z: 489 (M⁺).
IR (KBr): v/cm⁻¹: 3323 (br); 1697; 1620; 1571; 1253; 760.

EXAMPLE 8
3,3'-(4-carboxybenzylidene)bis[4,5,7-trihidroxycoumarin]

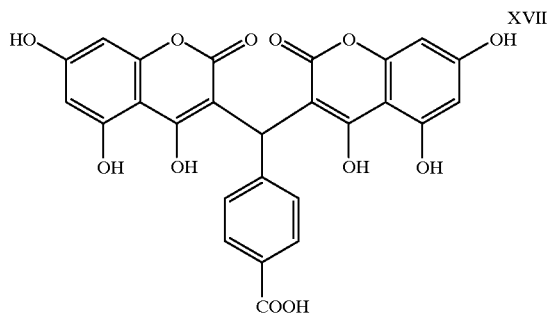
XVII

To a solution of 4,5,7-trihidroxycoumarin (2.00 g; 10.3 mmol) in 96% ethanol (10.0 ml) terephthalaldehyde acid (0.85 g; 5.67 mmol) was added. The reaction mixture was heated at boiling temperature for 12 hours. After cooling to room temperature the reaction mixture was evaporated to one half of its volume and left overnight at −13° C. and then water (20.0 ml) was added under stirring and under cooling with ice from exterior. The obtained precipitate was filtered in vacuo (1.80 g; 67%). M.p. 278–280° C.

Analysis:

calculated for $C_{26}H_{16}O_{12}$: C=60.01; H=3.10.

found: C=59.73; H=3.34.

FABMS: m/z: 521 (M⁺).

IR (KBr): v/cm⁻¹: 3420 (br); 1697; 1662; 1609; 1285; 760.

We claim:

1. Polyhydroxy derivative of coumarin fused with a dialdehyde acid of the general formula II:

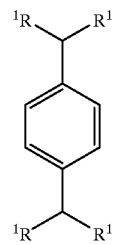
II wherein in formula II $R^1$ is 4,5,7-trihydroxycoumarin.

2. Polyhydroxy derivative of coumarin fused with a dialdehyde acid of the general formula II:

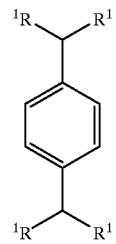
II wherein in formula II $R^1$ is 4,5,7-trihydroxycoumarin and wherein the derivative exhibits an antiviral action against HIV-1 virus.

* * * * *